United States Patent [19]

Kelly et al.

[11] Patent Number: 4,824,827

[45] Date of Patent: Apr. 25, 1989

[54] TIME-COLOR INDICATORS

[75] Inventors: Petrina M. Kelly, Egham; Colin Berrido, Bagshot, both of England

[73] Assignee: S. C. Johnson & Son, Inc., Racine, Wis.

[21] Appl. No.: 152,733

[22] Filed: Feb. 5, 1988

[30] Foreign Application Priority Data

Sep. 23, 1987 [GB] United Kingdom ............... 8722379

[51] Int. Cl.$^4$ ................................................ A61K 7/46
[52] U.S. Cl. ..................................... 512/1; 512/2; 422/75; 424/76.4
[58] Field of Search .................... 512/1, 2, 8, 25, ; 424/7, 1, 76.4; 422/75

[56] References Cited

U.S. PATENT DOCUMENTS

| | | | |
|---|---|---|---|
| 2,449,274 | 9/1948 | Broll | 422/56 |
| 3,480,402 | 11/1966 | Jackson | 424/56 |
| 3,996,007 | 12/1976 | Fang et al. | |
| 4,028,876 | 6/1977 | Delatorre | 422/57 |
| 4,062,649 | 12/1977 | Kuderna et al. | 512/1 |
| 4,128,508 | 12/1978 | Munden | 512/1 |
| 4,195,055 | 3/1980 | Patel | 422/56 |
| 4,195,056 | 3/1980 | Patel | 422/56 |
| 4,195,057 | 3/1980 | Patel | 422/56 |
| 4,200,606 | 4/1980 | Kitko | 422/37 |
| 4,212,153 | 7/1980 | Kydonieus et al. | 368/62 |
| 4,246,129 | 1/1981 | Kacher | 252/90 |
| 4,248,597 | 2/1981 | McNeely | 116/206 |
| 4,248,827 | 2/1981 | Kitko | 422/37 |
| 4,349,509 | 9/1982 | Yoshikawa et al. | 422/57 |
| 4,356,969 | 11/1982 | Obermayer et al. | 239/6 |
| 4,386,979 | 6/1983 | Jackson, Jr. | 149/21 |
| 4,678,658 | 7/1987 | Casey et al. | 424/7.1 |

FOREIGN PATENT DOCUMENTS 0095381 5/1985 Japan ................... 424/7.1

Primary Examiner—Werren B. Lone

[57] ABSTRACT

Disclosed are end point indicator compositions and devices containing them, particularly useful as air freshener devices, comprise compositions containing a polar indicator dye which assumes a first color or is colorless in the presence of a room temperature volatilizable solvent which is initially present in excess and a small amount of a proton donating compound. The indicator dye assumes a second color visually distinct from the first color in the presence of the proton donating compound after the majority of the solvent escapes from the remainder of the composition. Optionally, the compositions further include color change developers and/or secondary dyes to render the change to the second color, indicating attainment of the end point, more apparent to a user.

27 Claims, No Drawings

TIME-COLOR INDICATORS

BACKGROUND OF THE INVENTION

1. Field of the Invention

This invention relates to an end point indicator composition, particularly for air fresheners, which allows the user to determine whether an associated product is still effective by visually inspecting the product.

This invention further relates to the use of an indicator composition which includes a polar indicator dye which assumes a first color or is colorless in the presence of a volatile solvent which is initially present in excess. The indicator composition further includes a small amount of a proton donating compound wherein the indicator dye assumes a second color visually distinct from the first in the presence of that compound. The dye progressively assumes the second color as the solvent evaporates until when the second color is at its highest intensity, the solvent is essentially exhausted and the associated product should be replaced.

2. Description of the Prior Art

Kydonieus et al., U.S. Pat. No. 4,212,153 discloses a laminated indicator which changes in a visually perceptible mode with the passage of time and a method of making such an indicator. The indicator of Kydonieus et al. includes the migration of a dye or the migration of an acid or base within the laminated structure so that it is carried with the evaporation or the use of the product so that when the product is completely used up, the dye is visible to the user. The time-color indicator of Kydonieus et al. is dependent upon the pH of the solution. After the solvent substrate is exhausted, a pH change occurs whereby, for example, the substrate turns from acidic to basic and the color is elicited, thereby alerting the user that the composition is exhausted.

In another embodiment, there is a migration of the dye through various substrates along with the perfumes or fragrances whereby the dye builds up upon a polyester film and when the fragrance is exhausted, the dye is built up to a point where it is visible to the user.

The present invention differs from Kydonieus et al. in that it does not rely on the migration of an acid or base through at least two layers to cause a pH change which provides a visual color change perceptible to the user. The present invention relies on the change in concentration of a solvent relative to a polar proton donating compound to visually indicate an end point of a product. When the solvent is at its lowest concentration in the present invention, the proton donating compound is at its highest concentration and thus the second color is at its highest intensity. The present invention requires no multiple layers and also provides an indicator composition which can be visually transparent to a user.

Munden in U.S. Pat. No. 4,128,508 relates to a color change perfume system in which the color changes when the perfume is effectively exhausted into the atmosphere. Munden also teaches air fresheners consisting of porous carriers impregnated with the perfume coloring system.

Munden differs from the present invention in that it requires voltatile acid or base and a pH indicator whereby the acid or base volatilizes at the same rate as the perfume. The pH indicator changes color when the acid or base, and thus the perfume, is essentially exhausted from the system. Munden also contemplates use of aqueous systems although he mentions that the system can be made up largely of the essential components. The indicator composition of the present invention is nonaqueous and requires a combination of a major amount of a nonaqueous solvent, a minor amount of a proton donating compound which can be an ester, a dye and a perfume, none of which are required to be acidic or basic.

McNeely in U.S. Pat. No. 4,248,597 is a time watch or depletion indicator for removable substances and relies on a pH indicator in close proximity to the substance to be delivered. As the substance being delivered passes through a permeable membrane or porous substrate, as in Example 1 of McNeely, a pH change occurs and the color of the pH indicator changes and indicates that the substance being delivered is exhausted. McNeely relies on pH changes and pH indicator compounds to signal the user when depletion occurs. As noted above, the present invention does not require that an acidic or basic compound be present, but requires that both a solvent and a proton donating compound be present, as well as a polar dye, where the dye has one color in the solvent and a second color in the presence of the proton donating compound.

SUMMARY OF THE INVENTION

The present invention relates to the use of an indicator composition which includes an effective amount, preferably at least 0.0002% of the total weight of the composition, of a polar indicator dye which assumes a first color, or preferably is colorless, in the presence of a room temperature volatilizable nonaqueous solvent which is initially present in excess. The indicator composition further includes an effective amount, preferably at least 0.0002% of the total weight of the composition, of a proton donating compound such as linalyl acetate or a polyhydric alcohol wherein the indicator dye assumes a second color visually distinct from the first in the presence of that compound. The indicator dye progressively assumes the second color as the solvent evaporates and the concentration of the proton donating compound increases until when the second color is at its highest intensity or level of different from that of the first color, the solvent is essentially exhausted and the associated product should be replaced. The solvent is selected with the product to be depleted in mind so that the evaporation rate of the solvent substantially corresponds with the depletion rate of the product such as a perfume.

One advantage of the present invention is that although one can be present, the proton donating compound does not have to be an acid such as a carboxylic acid. It thus permits essentially neutral compositions to be made unlike other indicator systems which rely on pH changes such as basic to acidic to generate a color change. Other advantages of the present invention are that the composition are simple to manufacture and use, and provide a wide range of time spans by appropriate choice of solvents and means for releasing the same from the compositions.

The indicator dyes comtemplated for use are the Xanthene dyes, and particularly the Rhodamine dye series. In a preferred embodiment, a color change developer such as a 1,2-propylene glycol is included in an amount which is at least 0.005% by weight of the total composition to produce a more noticeable color change when the product is exhausted. In a more preferred embodiment, the indicator composition further includes an effective amount of a second dye which renders the second color change more apparent to a user.

DETAILED DESCRIPTION OF THE PREFERRED EMBODIMENT

Without wishing to be bound by any theory of operation, the following explanation is presented to assist others in positioning this invention. The present invention provides an indicator composition which comprises a polar indicator dye which assumes a color in the presence of a proton donating compound. The higher the concentration of the proton donating compound, the more the indicator dye becomes colored. By proper choice of a room temperature volatilizable nonaqueous solvent in which the indicator dye is soluble, the dye will assume a color different from the color exhibited in the presence of a proton donating solvent. More preferably, the dye is colorless in the presence of such a solvent. In the presence of the highly polar compound water, the indicator dye may remain strongly colored, even in the presence of a nonaqueous solvent. Therefore, aqueous solutions are to be avoided as are proton donating compounds which so strongly associate with the dye that they do not permit the indicator dye to assume a different color in the presence of a large amount of the solvent relative to the amount of the proton donating compound.

The present invention operates by balancing the ratio of the amount of solvent present versus the amount of proton donating compound present in the indicator composition in such a way that the indicator dye has a first or no color when the solvent is in excess and a second color when the solvent is depleted and the proton donating compound is present in a relatively high concentration. One simply matches the evaporation or release rate (if a membrane release method is employed) of the solvent to the escape rate of the product to be timed such as a perfume in an air freshener. The indicator dye is selected with the above characteristics in mind.

Thus, the present invention is restricted to use in a nonaqueous solvent solvent system and is not adapted for use in aqueous systems. This is due to the nature of the prior end point indicator dye which is, for example, a Xanthene dye, particularly, one selected from the Rhodamine dye series. The dye employed must be non-volatile at room temperature and sufficiently soluble in the solvent employed to permit it to assume a first color. That first color must be visually distinct from the color the dye assumes in the presence of a polar proton donating compound which is also sufficiently soluble in the solvent to be dispersed therein without settling out and carrying the indicator dye out of solution.

The dyes which are particularly useful are the colors classed chemically as Xanthene colors. These include N-[9-(2-Carboxyphenyl)-6-Diethylamino)-3H-Xanthen-3-ylidene]-N-Ethylethanaminium Chloride, commonly referred to as D & C Red No. 19 or Rhodamine B; and its free base N-[9-(2-Carboxyphenyl)-6-(Diethylamino)-3H-Xanthen-3-ylidene]-N-ethylethamine free base, commonly known as Solvent Red No. 49; N-[9-(2-Carboxyphenyl)-6-(Diethylamino)-3H-Xanthen-3-ylidene]-N-Ethylethanaminium Octadecanoate, commonly referred as D & C Red No. 37, Rhodamin-B-Stearate or D & C Red No. 49:1; the barium salt of D & C Red 37, the zirconium salt of D & C Red 37, and mixtures thereof. These dyes, when present in a very small amount of from 0.0002% (2 ppm=parts per million) by weight of the composition in a proton-donating solvent base are essentially colorless. The most preferred dyes are the oil soluble dyes are Solvent Red No. 49 followed by D & C Red No. 37. The maximum amount of dye is that amount which will permit a visible color change to be observed although generally 0.5% based on the total indicator composition is a practical upper limit with 0.02% (200 ppm) being a typical amount to be used. The amount of such a dye necessary will also be governed by the nature of the dye and total composition as well as the amount of a second dye added to render the color change more apparent to a user as will be discussed below.

Suitable solvents are room temperature volatilizable nonaqueous solvents in which the indicator dye or dyes selected are soluble and wherein the dye assumes a first color, or is preferably colorless, when the indicator dye or dyes are dissolved therein. For use in air freshener compositions, the solvents should not impart adverse odors to the air freshening fragrance released and should not substantially adversely affect the effectiveness of the fragrances used in such compositions. The solvents employed in air freshener compositions may also serve to assist in bringing about the desired fragrance such as where fragrance esters are employed. Examples of suitable nonaqueous solvents are isobornyl acetate, benzyl acetate and hydrocarbon terpene blends, depending upon the dye used as shown in Example 1 below.

As noted in Example 3, certain alcohols and ketones are capable of dissolving dyes such as Solvent Red No. 49 without generating a color change and can thus serve as solvents if the evaporation rate of such solvents is comparable to the rate at which the product associated with the composition is exhausted.

The solvent is present in a sufficient excess over the amount of proton donating compound present to cause the dye to assume and retain its first color until a substantial portion of the solvent is removed from contact with the rest of the indicator composition such as by evaporation or permeation through a membrane. Non-polar and/or non-proton donating solvents are preferred since a proton donating compound is employed to induce a second color in the indicator dye.

A suitable proton donating compound is one which is soluble in the solvent or solvents selected for use in the indicator composition and in which the indicator dye assumes a second color different from the color it possesses in the presence of the first solvent. Proton donating compounds found to be useful with several Rhodamine dyes tested are organic esters such as linalyl acetate and benzyl acetate, see Example 1 below, and compounds containing multiple hydroxyl radicals such as certain polyhydric alcohols which are described below as being useful as color change developers, such as 1,2-propylene glycol and glycerol. Hydroxylated polymers such as polysaccharides may also be useful as proton donating compounds. The proton donating compound must be less volatile from the solvent so that a sufficient amount is present to cause the second color to appear when the solvent has substantially left the indicator composition. Organic acids may find use as proton donating compounds, but are less preferred. Certain esters may hydrolyze to form acids and that may account for some of their utility as proton donating compounds, but see Example 3. Preferably, the proton donating compounds are present in an amount which is at least 0.0002% of the total weight of the indicator composition and the amount used is less than that amount which would cause the second color to appear initially and thus render the time-color indicator aspect of the composition ineffective. The amount of indicator dye must be balanced with the amount of proton donating compound since higher amounts of dye can result in intense colors even when a small amount of proton donating compound is present. Generally, no more than about 20% of the total indicator composition is proton donating compound. The actual maximum amount of each component will depend on the amount of indicator dye and proton donating compound as well as the amount of solvent since there must be enough solvent to prevent a color change to the second color until the solvent is substantially exhausted or the product associated therewith has become ineffective.

For example, many well known perfume compositions contain a mixture of room temperature volatilizable solvents and proton donating compounds to which an indicator dye of the type described above can be added. The fragrance imparting material present in the perfume composition, i.e. essential oils, evaporate at about the same rate as do the solvents and other volatile materials present in the perfume compositions. Thus, when the concentration of the volatile solvents and essential oils becomes sufficiently low, there is often a sufficient level of proton donating compound present to cause the indicator dye to assume a second color visually distinct from the first. Perfume compositions suitable for air freshener use are well known and are commercially available from fragrance houses such as Firmenich, S. A. of Geneva, Switzerland, and International Flavors and Fragrances, Inc., of New York, NY.

The time-color indicator compositions of the present invention can be applied to felt pads or other porous substrates which are then sealed within containers of impervious materials such as metal foil to prevent premature evaporation of the solvent until the article to be used. Compositions of the present invention can be enclosed in membrane vapor dispensing devices of the type described in U.S. Pat. Nos. 4,534,820 to Holzner and 4,558,820 to Harris which are hereby incorporated by reference to teach devices containing permeable membranes to release the solvent, and optionally, a fragrance imparting material at the same time. Without a fragrance imparting material present, the membrane device can simply be used as a timer since the color will change when the solvent is substantially released to the atmosphere. The release rate is controlled by the nature and thickness of the membrane device in a known manner.

The color change of the indicator dye may be rendered more noticeable by the addition of a small amount of a color change developer in the nature of a polyhydric alcohol. Suitable color change developers are those such as 1,2-propylene glycol, dipropylene glycol, glycerol, triethylene glycol and mixtures thereof. The color change developers should be present in an amount of at least 0.0005% by weight (5 ppm) based on the total amount of indicator composition and more preferably between 0.001% (10 ppm) to 0.01% (100 ppm) by weight of the total indicator composition. These color change developers can also be used as the proton donating compound in the compositions of the present invention.

In a still more preferred embodiment, the indicator composition further contains an effective amount of a second dye which colors the indicator composition initially and renders the color change of the indicator dye more apparent to the user. Any number of dyes could be employed provided that the dye is soluble in the indicator composition and does not mask the fact that a color change has occurred when the solvent has substantially left the composition. Examples of useful dyes are 1,4-Bis[(4-Methylphenyl)Amino-9,10-Anthracendione] commonly known as Solvent Green 3 and monoazo dye, Color Index Constitution No. 12740, or Chemical Abstracts Service (CAS) Registry No. 6407-78-9 and commonly known as Solvent Yellow 18.

For example, the combination of 0.0002% (2 ppm) Solvent Red No. 49 as an indicator dye with 0.0004% (4 ppm) Solvent Yellow No. 18 and 0.0005% (5 ppm) Solvent Green No. 3 as secondary dyes resulted in an air freshening indicator composition of the present invention produced a composition sealed in a transparent semipermeable ethylene/vinyl acetate copolymer pouch which was initially light green in color and turned brown/pink after the composition was placed in an oven for five days at 38° C. to essentially exhaust the solvent and fragrance imparting material from the composition (See Example 18). The same composition made without the secondary dyes was almost colorless with a light gold tint initially and was fluorescent pink after five days at 38° C. A more preferred higher level of dyes is that employed in Example 44: 0.02% (200 ppm) Solvent Red No. 49, 0.005% (50 ppm) Solvent Green 3 and 0.004% (40 ppm) Solvent Yellow 18.

The present invention has been described with specific reference to air freshening compositions. However, it is understood that it can be used in other applications where a product associated with the indicator composition becomes depleted over a period of time such as controlled release insecticide products. The time-color indicator compositions may be separately packaged and affixed to a product which is to be replaced after a certain period of time such as an air filter in a home furnace or above a stove or oven. Those skilled in the art will readily appreciate other uses for the compositions of the present invention upon reviewing the above description and the Examples.

The following Examples are provided to show various aspects of the present invention without departing from the scope and spirit of the invention. Unless otherwise indicated, all parts and percentages used in this specification are by weight.

In the Examples, three perfume compositions were employed comprising fragrance imparting materials and solvents (which also impart a fragrance to the composition) which are described below. The nature of the fragrance imparting materials was proprietary to the manufacturer, but was believed to contain essential oils acting as perfumes along with other solvents and diluents. Each composition initially exhibited a slight or no color when Solvent Red No. 49 and D & C Red No. 37 was added and a second color when most of the perfume composition evaporated away leaving the dye and a residue behind.

|  | Perfume Composition | | |
| --- | --- | --- | --- |
|  | A | B | C |
| Fragrance Imparting Material | 24 | 35.5 | 22.5 |
| Hydrocarbon Terpenes | 32 | 18 | 34 |
| Benzyl Acetate | 27 | 3 | 30 |
| Linalyl Acetate | 4 | 0.5 | 13 |

-continued

|  | Perfume Composition | | |
| --- | --- | --- | --- |
|  | A | B | C |
| Isobornyl Acetate | 13 | 43 | 0.5 |

The following are chemical names or further references for the dyes used in the Examples which were not already defined above:

D & C Green No. 8—8-Hydroxy-1,3,6-Pyrenetrisulfonic Acid, Trisodium Salt

D & C Red No. 22—Spiro[Isobenzofuran-1(3H),9'-[9H]Xanthen]-3-one, 2',4',5',7'-[9H]Xanthen]-3-one, disodium salt Rhodamine 6G (Basic Red No. 1)—CAS Registry No. 989-38-8 or C.I. (Color Index) No. 45160

Uranine (D & C Yellow No. 8)—3',6'-Dihydroxyspiro[Isobenzofuran-1(3H), 9'[9H]Xanthen]-3-one, Disodium Salt Pyronine—N-[6-(Dimethyl)amino)-3H-xanthen-3-ylidene]-N-methylmethanaminum chloride Erythrosine (FD & C Red No. 3)—Spiro[Isobenzofuran-1-(3H),9'[9H]Xanthen]-3-one, 3'6'-Dihydroxy-2',4',5',7'-tetraiodo-, Disodium Salt Basic Yellow 40—CAS Registry No. 12221-86-2

Solvent Yellow 43—CAS Registry No. 12226-96-9

Rhodamine B (Basic Violet 10)—N-[9-(2-Carboxyphenyl)-6-(Diethylamino)-3H-Xanthen-3-ylidene]-N-Ethylethanaminium Chloride

EXAMPLE 1

In this Example, perfume compositions containing Solvent Red No. 49 as an indicator dye were placed on paper pads to show that a color change was observed as the perfume composition evaporated from the pad.

In Example 1A, 0.02% Solvent Red No. 49 was added to Perfume Composition A to make an end point indicating air freshener composition. The end point indicating air freshener composition of Example 1B was Perfume Composition A containing 0.002% Solvent Red No. 49.

3 grams of each composition was added to an absorbent paper pad which was then placed in a holder with the paper pad exposed to the atmosphere. The pad of Experiment 1A initially had a pink color, while the pad of Experiment 1B, which contained one-tenth of the dye present in Experiment 1A, was observed to have a pale pinky/orange color. After 8 days at room temperature, both pads were observed to have slightly increased in pink coloration indicating to the user that the perfume composition had decreased in concentration.

EXAMPLE 2

In this Example, the effect of the major solvents present in Perfume Compositions A-C on certain xanthene dyes was tested. The solubility of the dye in each solvent, the colors observed and the appearance of the dye after the solvent was evaporated away ("Dry" in Table I) were observed and the results are recorded in Table I.

TABLE I

| DYE | ISOBORNYL ACETATE | LINALYL ACETATE | HYDROCARBON TERPENES | BENZYL ACETATE |
| --- | --- | --- | --- | --- |
| D & C Green #8 | ss-Pale Yellow | ss-Pale Yellow | ? | vss-Very Pale Yellow |
|  | Dry-No Color | Dry-No Color | Dry-No Color | Dry-No Color |
| D & C Red #22 | ss-Pale Red | ss-Fl Orange | ss-Tinge Red | ss-Fl Pink |
|  | Dry-No Color | Dry-No Color | Dry-No Color | Dry-No Color |
| D & C Red #19 | vss-Black Tinge | Fs-Fl Pink | ? | s-Fl Dark Pink |
|  | Dry-Slight Pink | Dry-Pink | Dry-No Color | Dry-Pale Pink |
| D & C Red #37 | s-Colorless | S-Fl Pink | ss-Tinge Red | s-Colorless |
|  | Dry-Pink | Dry-Pink | Dry-Circle of Dark Pink | Dry-Pink |
| Solvent Red #49 | S-Tinted | S-Fl Pink | ss-Tinge color | s-Almost Colorless |
|  | Dry-Dark Pink | Dry-Pink | Dry-Circle of Dark Pink | Dry-Pink |
| Ryodamine 6G (Basic Red #1) | ss-Dull Pink | SS-Fl Orange | vss-Dulled Color | ss-Fl Pink |
|  | Dry-Very Pale Pink | Dry-Bright Peach Pink | Dry-Very Pale Pink | Dry-Small Circle of Pink |
| Uranine (D & C Yellow #8) | vss-Orange Tinge | ns | ? | ss-Very Pale Orange |
|  | Dry-No Color | Dry-No Color | Dry-No Color | Dry-No Color |
| Pyronine | NS | NS | ? | NS |
|  | Dry-No Color | Dry-No Color | Dry-No Color | Dry-No Color |
| Erythrosine (FD & C Red #3) | ss-Pink | ss-Orange | ? | ss-Deep Pink |
|  | Dry-No Color | Dry-No Color | Dry-No Color | Dry-No Color |
| Basic Yellow 40 | ss-Pale Fl Green | S-Fl Green | ? | s-Fl Green |
|  | Dry-No Color | Dry-Pale Green | Dry-No Color | Dry-Yellow |
| Solvent Yellow 43 | s-Bright Fl Green | s-Bright Fl Green | s-No Color | s-Bright Fl Green |
|  | Dry-Pale Yellow | Dry-Very Pale Yellow | Dry-Pale Yellow | Dry-Pale Yellow |
| Rhodamine B (Basic Violet 10) | ss-Very Pale Pink | ss-Fl Pink | ? | ss-Fl Dark Pink |
|  | Dry-No Color | Dry-Pink | Dry-Very Pale Pink | Dry-Pale Pink | s = soluble;
ss = slightly soluble;
fs = fairly soluble;
vss = very slightly soluble;
ns = not soluble;
fl = fluorescent; and
= No.
? = Appeared insoluble, but deep yellow of solvent was thought to hide and slight color change.

As can be seen in TABLE I, certain dyes were not affected by the solvents tested such as D & C Green No. 8 which was, at best, slightly soluble in several of the solvents and pyronine, which was insoluble in the solvents tested. The most desirable dyes to employ are those which are soluble in certain solvents in which they possess one color and are at least slightly soluble in other compounds which cause the dye to assume a color different from that exhibited in the first solvent. The Xanthene colors of the Rhodomine series, such as Solvent Red No. 49 and D & C Red No. 37, fit this requirement since they are brightly colored by linalyl acetate, but are soluble in the other two acetate solvents with little or no color present.

Other Rhodamine dyes which were slightly soluble, but had different colors in different solvents, were D & C Red Nos. 19 and 22, Rhodamine B and Rhodamine 6G. Since only very small quantities of dye are necessary to carry out the invention, slight solubility may be adequate or a combination of solvents can be employed to improve the solubility of the indicator dye.

Solvent Yellow 43 was found to be brightly colored green and soluble in each of the acetates evaluated, but soluble and pale yellow in hydrocarbon terpenes solvent, thus suggesting that an indicator composition employing hydrocarbon terpenes as the major amount of nonaqueous solvent and one of the acetates as a proton donating compound could be made using Solvent Yellow 43 as the indicator dye.

Uranine seemed to behave similar to D & C Green No. 8 for the solvents tested, while Basic Yellow 40 retained the same color for all those solvents in which it was soluble. Erythrosine was slightly soluble in isobornyl acetate and benzyl acetate in which it had a pink color, while it was orange in linalyl acetate. This suggests a possible combination of solvents and proton donating compounds for this dye to be used in the present invention: use of an excess of isobornyl acetate and/or benzyl acetate as a nonaqueous solvent with a small amount of linalyl acetate as a proton donating compound.

EXAMPLE 3

In this Example, a number of potential proton donating compounds were tested for production of color in Solvent Red No. 49. A base solution containing 0.01% Solvent Red No. 49 in a nonaqueous solvent, Isopar H, was prepared. Isopar H is a mixture of branched chain aliphatic hydrocarbons with 11 or 12 carbons in the alkyl chain sold by Esso. One percent of each of the following compounds were added to the above base solution and the solution was observed for the development of color.

| COMPOUND | COLOR |
| --- | --- |
| Acetone | Colorless |
| Ethyl Acetate | Colorless |
| Acetic Acid | Red |
| Methanol | Red |
| Ethanol | Red |
| n-Propanol | Colorless |
| n-Butanol | Colorless |
| n-Pentanol | Colorless |
| 1,2-Propylene Glycol | Very Intense Red |
| Glycerol | Very Intense Red |

Surprisingly, ethyl acetate was found to be inactive as a potential proton donating compound as was acetone. Acetic acid, methanol and ethanol were all found to generate a red color with the dye, however, the color tended to stay red even in the presence of a large excess of solvent making such compounds much less desirable for use in the present invention. The higher homologues of the series of alcohols, n-propanol, n-butanol and n-pentanol, tested were inactive with respect to the dye. The more highly hydroxylated 1,2-propylene glycol and glycerol were found to produce very intense red colors. This property was found to be of value where they were added to compositions of the present invention as color change developers.

EXAMPLES 4-21

In these Examples, time-color indicating air freshener compositions of the present invention were made and placed in semipermeable membrane sachets to demonstrate the color change of compositions containing minimal amounts of indicator dye. Some of the Examples further contained secondary dyes to make the color change more apparent to the user.

Time-color indicator compositions were prepared as described in TABLE II using the stated percentages of Perfume Compositions A, B, or C, Red Dye No. 49 or D & C Red No. 37 as an indicator dye and, in Examples 16-21, Solvent Yellow 18 or Solvent Yellow 18 plus Solvent Green 3 as secondary dyes.

About 5 cubic centimeters of each composition was heat sealed within a transparent ethylene/vinyl-acetate copolymer flexible film pouch having a wall thickness of 150 microns to make a controlled release air freshener sachet and the initial color of the composition was recorded. The walls of the pouch were permeable to the solvents and essential oils contained within the perfume compositions and permitted the slow release of fragrance over an extended period of time at room temperature. To accelerate the release of the fragrance, each sachet was hung from a rack and placed in a hot room at 38° C. The color of the contents of each sachet was observed after four days and after five days at 38° C. when a significant amount of the perfume compound has been released. The results obtained are found in Table II.

In general, 0.0002% was about the minimum level of indicator dye to show a noticeable change, although a small change was noticeable at an indicator dye level of 0.00002% (0.2 ppm). The color change was more pronounced for perfume compositions A and C than for perfume composition B. The use of a single secondary dye in Examples 16-17 resulted in a slightly different shade of color after 5 days at 38° C., while inclusion of two secondary dyes in Examples 18-21 causes the initial color to be green and results in a significantly different end point color.

TABLE II

| Ex. | PC | PC Amount | Solvent Red No. 49 | D & C Red No. 37 | Solvent Green 3 | Solvent Yellow 18 | Initial Color | 4 Days @ 38° C. | 5 Days @ 38° C. |
| --- | --- | --- | --- | --- | --- | --- | --- | --- | --- |
| 4 | A | 99.9998 | 0.0002 | — | — | — | Golden Yellow | Orange/Red | Orange/Red |
| 5 | A | 99.99998 | 0.00002 | — | — | — | Golden Yellow | Golden Yellow | Yellow |
| 6 | B | 99.9998 | 0.0002 | — | — | — | Colorless | Pink | Pink |
| 7 | B | 99.99998 | 0.00002 | — | — | — | Colorless | Golden Yellow | Yellow |
| 8 | C | 99.9998 | 0.0002 | — | — | — | Light Gold/Colorless | Fluorescent Pink | Fluorescent Pink |
| 9 | C | 99.99998 | 0.00002 | — | — | — | Light Gold/Colorless | Golden Yellow | Yellow |
| 10 | A | 99.9998 | — | 0.0002 | — | — | Golden Yellow | Golden Yellow | Yellow Orange |
| 11 | A | 99.99998 | — | 0.00002 | — | — | Golden Yellow | Golden Yellow | Yellow |
| 12 | B | 99.9998 | — | 0.0002 | — | — | Colorless | Very Faint Pink | Faint Pink |
| 13 | B | 99.99998 | — | 0.00002 | — | — | Colorless | Faint Yellow | Yellow |
| 14 | C | 99.9998 | — | 0.0002 | — | — | Light Golden Yellow | Fluorescent Pink | Fluorescent Pink |
| 15 | C | 99.99998 | — | 0.00002 | — | — | Light Golden Yellow | Golden Yellow | Yellow |
| 16 | A | 99.9994 | 0.0002 | — | — | 0.0004 | Darker Golden Yellow | Yellow/Orange | Orange |
| 17 | A | 99.99994 | 0.00002 | — | — | 0.00004 | Darker Golden Yellow | Yellow | Yellow |
| 18 | C | 99.9989 | 0.0002 | — | 0.0005 | 0.0004 | Pale Green | Brown/Pink | Brown/Pink |
| 19 | C | 99.99908 | 0.00002 | — | 0.0005 | 0.0004 | Pale Green | Pale Green | Pale Green |
| 20 | C | 99.9989 | — | 0.0002 | 0.0005 | 0.0004 | Pale Green | Grey/Green | Brown/Green |
| 21 | C | 99.99908 | — | 0.00002 | 0.0005 | 0.0004 | Pale Green | Green | Light Brown/Green |

PC = Perfume Composition

EXAMPLES 22–29

In these Examples, a color-change developer compound, 1,2-propylene glycol, was included in an end point indicating air frshener compositions to provide a more dramatic end point color change.

Perfume Composition B was used in these Examples, along with two levels of either Solvent Red No. 49 or D & C Red No. 37 and two levels of 1,2-propylene glycol. Two levels of 1,2-monopropylene glycol were used since the intensity of the color developed depends upon that level, as well as the amount of indicator dye. It is desirable to use the minimum amount of indicator dye and color developer so that the maximum color change occurs at about the point where the perfume composition is essentially exhausted. Early, intense color development is to be avoided since this could be interpreted as an end point signal before the perfume composition is essentially exhausted.

The compositions are described in Table III in terms of percentages employed and 5 cubic centimeters of each composition were heat sealed into pouches as described for Examples 4–21 to make sachets. The sachets were placed in a hot room at 38° C. All samples were initially colorless and the results observed after 1 day and 6 days at 38° C. are reported in Table III.

TABLE III

| Ex. | PC | PC Amount | Solvent Red No. 49 | D & C Red No. 7 | 1,2-propylene glycol | Initial Color | 1 Day @ 38° C. | 6 Days @ 38° C. |
| --- | --- | --- | --- | --- | --- | --- | --- | --- |
| 22 | B | 99.970 | 0.02 | — | 0.01 | Colorless | Deep Pink | Deep Pink |
| 23 | B | 99.988 | 0 002 | — | 0.01 | Colorless | Pale Pink | Pale Pink |
| 24 | B | 99.979 | 0.02 | — | 0.001 | Colorless | Deep Pink | Deep Pink |
| 25 | B | 99.997 | 0.002 | — | 0.001 | Colorless | Pale Pink | Pale Pink |
| 26 | B | 99.970 | — | 0.02 | 0.01 | Colorless | Very Pale Pink | Deep Pink |
| 27 | B | 99.988 | — | 0.002 | 0.01 | Colorless | Very Pale Pink | Very Pale Pink |
| 28 | B | 99.979 | — | 0.02 | 0.001 | Colorless | Pale Pink | Deep Pink |
| 29 | B | 99.997 | — | 0.002 | 0.001 | Colorless | Colorless | Pale Pink |

PC = Perfume Composition.

Examples 26 and 28 seemed to give the best results for this series since only a pale pink color developed after one day, while a deep pink color was observed after six days when the sachet had released a significant amount of perfume.

EXAMPLES 30–47

In these Examples, end point indicating air freshener compositions were prepared as in Examples 4–21, but using higher levels of indicator dyes. The percentages of each component of the compositions are reported in TABLE IV. Sachets were prepared and placed in a hot room using the procedure described in Examples 4–21, but the colors developed were observed after one day and six days at 38° C. The results are reported in TABLE IV.

TABLE IV

| Ex. | PC | PC Amt. | Solvent Red | D & C Red No. 49 | Solvent Green 3 | Solvent Yellow 1 | Initial Color | 1 Day @ 38° C. | 6 Days @° C. |
| --- | --- | --- | --- | --- | --- | --- | --- | --- | --- |
| 30 | A | 99.98 | 0.02 | — | — | — | Dark Pink/Orange | Very Dark Pink | Bright Pink |
| 31 | A | 99.998 | 0.002 | — | — | — | Golden Yellow | Orange/Pink | Pale Pink |
| 32 | B | 99.98 | 0.02 | — | — | — | Salmon | Very Red Pink | Pink |
| 33 | B | 99.998 | 0.002 | — | — | — | Gold | Pale Orange/Pink | Pale Pink |
| 34 | C | 99.98 | 0.02 | — | — | — | Pink | Very Deep Pink | Very Deep Fluorescent Pink |
| 35 | C | 99.998 | 0.002 | — | — | — | Light Pink | Pale Orange/Pink | Fluorescent Pink |
| 36 | A | 99.98 | — | 0.02 | — | — | Gold | Pale Orange/Pink | Pink |
| 37 | A | 99.998 | — | 0.002 | — | — | Light Gold | Very Pale Orange/Yellow | Orange Pink |
| 38 | B | 99.98 | — | 0.02 | — | — | Colorless | Pale Pink | Pink |
| 39 | B | 99.998 | — | 0.002 | — | — | Colorless | Very Pale Pink | Pale Pink |

TABLE IV-continued

| Ex. | PC | PC Amt. | Solvent Red | D & C Red No. 49 | Solvent Green 3 | Solvent Yellow 1 | Initial Color | 1 Day @ 38° C. | 6 Days @ ° C. |
|---|---|---|---|---|---|---|---|---|---|
| 40 | C | 99.98 | — | 0.02 | — | — | Pink | Very Dark Pink | Bright Pink |
| 41 | C | 99.998 | — | 0.002 | — | — | Pale Pink | Pale Orange | Fluorescent Pink |
| 42 | A | 99.976 | 0.02 | — | — | 0.004 | Orange | Orange Pink | Red/Pink |
| 43 | A | 99.994 | 0.002 | — | — | 0.004 | Light Orange | Yellow | Orange with Red Edges |
| 44 | C | 99.971 | 0.02 | — | 0.005 | 0.004 | Brown with Pink Edges | Pink/Gray-Green | Dark Green/Red |
| 45 | A | 99.976 | — | 0.02 | — | 0.004 | Orange | Orange/Red Developing | Orange with Red Edges |
| 46 | A | 99.994 | — | 0.002 | — | 0.004 | Orange Yellow | Yellow | Yellow with Pink Edges |
| 47 | C | 99.971 | — | 0.02 | 0.005 | 0.004 | Brown/Green | Red Color Developing | Brown/Red |

PC = Perfume Composition

TABLE IV shows the different in end point colors obtained when Perfume Compositions A–C, which contained different levels of linalyl acetate, a proton donating compound for the indicator dyes tested. Other components present in the proprietary Fragrance Importing Material may also have acted as porton donating compounds and contributed to color development. Examples 30, 32 and 34 using Solvent Red No. 49 only differed in Perfume Composition, but exhibited different color intensities as did Examples 36, 38 and 40 which employed D & C Red No. 37. The same is true for Examples 42–47 which employed secondary dyes. Compositions of the type employed in Examples 44 and 47 were also prepared using Perfume Compositions A and B, but the color change from initial to six days was not significantly different enough to serve as end point indicating compositions.

EXAMPLE 48

In this Example, an end point indicating air freshener composition was sealed into a permeable bag as in Examples 4–21 and the bag was placed in a vapor-dispensing device. The weight loss and color change of the composition as a function of time was observed by allowing it to remain exposed to the atmosphere at room temperature for forty days.

A perfume composition containing a nonaqueous solvent mixture and at least one proton donating compound was mixed with 0.015% of Solvent Red No. 49 and 5 cubic centimeters of the mixture (slightly less than 5 grams) was heat-sealed within the inner chamber of a flexible dispensing pouch as in Examples 4–21. The dispensing pouch was rectangular and formed of a transparent ethylene/ethyl acrylate copolymer (15% ethyl acrylate) film having a thickness of 150 to 180 microns through which the perfume composition would permeate. The rectangular pouch was enclosed within a frame between two grilles to flatten the pouch and to expose both sides of the copolymer film to the atmosphere. The color of the composition was observable through the grille openings.

The results observed were as follows:

| TIME (DAYS) | WEIGHT LOSS (GRAMS) | COLOR CHANGE |
|---|---|---|
| 0 | 0 | Colorless |
| 1 | 0.47 | Pink in Corners |
| 5 | 0.90 | Pink Top & Corners |
| 11 | 1.89 | One Quarter Covered Pink |
| 18 | 2.62 | One Third Covered Pink |
| 27 | 3.50 | Half Covered Pink |
| 40 | 4.53 | Totally Pink |

As the perfume composition was released from the device, as noted by the weight loss, the color of the composition within the rectangular pouch was observed to spread across the thin pouch until after forty days, the perfume composition was essentially exhausted.

We claim:

1. A time-color indicator composition to visually indicate when a product associated with said composition has become ineffective for its intended use, said composition comprising:
   (a) a room temperature volatilizable, nonaqueous liquid solvent;
   (b) an effective amount of an indicator dye which is substantially nonvolatile at room temperature and is soluble in said solvent, said dye assuming a first color when dissolved in said solvent; and
   (c) an effective amount of at least one proton donating compound wherein said dye assumes a second color visually distinct from said first color when the dye is in contact with only said compound, wherein the ratio of the solvent to the dye and the proton donating compound is such that upon evaporation of said solvent, said dye visually changes from said first color to said second color, assumption of said second color indicating that the product has become ineffective and wherein all components of said composition are selected to result in a composition which is essentially neutral in pH.

2. The composition of claim 1 wherein said dye is present in an amount of at least 0.0002% of the total weight of the composition, the proton donating compound is present in an amount of at least 0.0002% of the total weight of the composition and the solvent comprises the balance of the composition.

3. The composition of claim 1 wherein the dye is selected from Xanthene dyes selected from the group consisting of N-[9-(2-carboxyphenyl)-6-diethylamino-3H-Xanthen-3-ylidene]-N-Ethylethanaminium chloride, the free base of N-[9-(2-carboxyphenyl)-6-diethylamino-3H-Xanthen-3-ylidene]-N-Ethylethanaminium chloride, N-[9-(2-carboxyphenyl)-6-diethylamino-3H-Xanthen-3-ylidene]-N-Ethylethaniminium Octadecanoate, barium salts of N-[9-(2-carboxypheny)-6-diethylamino-3H-Xanthen-3-ylidene]-

N-Ethylethanaminium Octadecanaote, zirconium salts of N-[9-(2-carboxyphenyl)-6-diethylamino-3H-Xanthen-3-ylidene]-N-Ethylethanaminium Octadecanoate, and mixtures thereof.

4. The composition of claim 1 wherein the proton donating compound only contains proton donating radicals selected from the group consisting of hydroxyl and ester radicals.

5. The composition of claim 1 wherein the proton donating compound only contains hydroxyl radicals as the proton donating portion of the compound.

6. The composition of claim 1 which further includes at least 0.005 percent by weight based on the total weight of the composition of a color change developer selected from the group consisting of 1,2-propylene glycol, glycerol, dipropylene glycol, triethylene glycol and mixtures thereof.

7. The composition of claim 1 which further includes an effective amount of a second dye which renders the color change more apparent to a user.

8. The composition of claim 1 wherein said first color is substantially colorless to the eye.

9. The composition of claim 1 wherein said solvent comprises at least one solvent selected from the group consisting of isobornyl acetate, and hydrocarbon terpene blends.

10. An end point indicating air freshening composition which alerts a user by a color change when a perfume contained therein is essentially exhausted, said composition comprising:
   a. an effective amount of at least one proton donating compound;
   b. a room temperature volatilizable nonaqueous solvent;
   c. one or more fragrance imparting materials; and
   d. an effective amount of an indicator dye which is substantially nonvolatile at room temperature and is soluble in said solvent, said dye assuming a first color when dissolved in said solvent and assuming a second color, visually distinct from the first color when the dye is in contact with only said proton donating compound; wherein said solvent and said fragrance imparting materials are released at approximately the same rate and the ratio of the solvent to the dye and the proton donating compound is such that the dye assumes said first color when the fragrance imparting material is at its highest concentration and assumes the second color when substantially all of the fragrance imparting compound has been released, thereby visually indicating that the level of fragrance imparting material is ineffective and wherein all components of said composition are selected to result in a composition which is essentially neutral in pH.

11. The composition of claim 10 wherein said dye is present in an amount, based on the total weight of the air freshening composition, of at least 0.0002% and the proton donating compound is present in an amount of at least 0.0002%.

12. The composition of claim 10 wherein the dye is selected from Xanthene dyes selected from the group consisting of N-[9-(2-carboxyphenyl)-6-diethylamino-3H-Xanthen-3-ylidene]-N-Ethylethanaminium chloride, the free base of N-[9-(2-carboxyphenyl)-6-diethylamino-3H-Xanthen-3-ylidene]-N-Ethylethanaminium chloride, N-[9-(2-carboxyphenyl)-6-diethylamino-3H-Xanthen-3-ylidene]-N-Ethylethanaminium Octadecanoate, barium salts of N-[9-(2-carboxyphenyl)-6-diethylamino-3H-Xanthen-3-ylidene]-N-Ethylethanaminium Octadecanoate, zirconium salts of N-[9-(2-carboxyphenyl)-6-diethylamino-3H-Xanthen-3-ylidene]-N-Ethylethanaminium Octadecanoate, and mixtures thereof.

13. The composition of claim 10 wherein the proton donating compound only contains proton donating radicals selected from the group consisting of hydroxyl and ester radicals.

14. The composition of claim 10 wherein the proton donating compound only contains hydroxyl radicals as the proton donating portion of the compound.

15. The composition of claim 10 which further includes at least 0.005 percent by weight based on the total weight of the composition of a color change developer selected from the group consisting of 1,2-propylene glycol, glycerol, dipropylene glycol, triethylene glycol and mixtures thereof.

16. The composition of claim 10 which further includes an effective amount of a second dye which renders the color change more apparent to a user.

17. The composition of claim 10 wherein said first color is substantially colorless to the eye.

18. The composition of claim 10 wherein said solvent comprises at least one solvent selected from the group consisting of isobornyl acetate, and hydrocarbon terpene blends.

19. The composition of claim 10 wherein said solvent includes at least one solvent selected from the group consisting of isobornyl acetate and hydrocarbon terpene blends, the dye is N-[9-(2-carboxyphenyl)-6-diethylamino-3H-Xanthen-3-ylidene]-N-Ethylethanaminium Octadecanoate, and at least one of the proton donating compounds present is linalyl acetate.

20. The composition of claim 19 which further includes at least 0.005 percent by weight based on the total weight of the composition of a color change developer selected from the group consisting of 1,2-propylene glycol, glycerol, dipropylene glycol, triethylene glycol and mixtures thereof.

21. A time-color indicator device comprising the composition of claim 1 enclosed within a sealed container having a membrane thereon which permits said solvent to permeate through the membrane at a controlled rate.

22. An air freshening device comprising the composition of claim 1 enclosed within a sealed container having a membrane thereon which permits the solvent and fragrance imparting material to be released at similar controlled rates.

23. The composition of claim 3 wherein said dye is present in an amount of at least 0.0002% of the total weight of the composition, the proton donating compound only contains proton donating radicals selected from the group consisting of hydroxyl and ester radicals and is present in an amount of at least 0.0002% of the total weight of the composition and the solvent comprises the balance of the composition.

24. The composition of claim 23 which further includes at least 0.005 percent by weight based on the total weight of the composition of a color change developer selected from the group consisting of 1,2-propylene glycol, glycerol, dipropylene glycol, triethylene glycol and mixtures thereof.

25. The composition of claim 12 wherein said dye is present in an amount of at least 0.0002% of the total weight of the composition, the proton donating compound only contains proton donating radicals selected from the group consisting of hydroxyl and ester radicals and is present in an amount of at least 0.0002% of the total weight of the composition and the solvent comprises the balance of the composition.

26. The composition of claim 25 which further includes at least 0.005 percent by weight based on the total weight of the composition of color change developer selected from the group consisting of 1,2-propylene glycol, glycerol, dipropylene glycol, triethylene glycol and mixtures thereof.

27. The composition of claim 25 wherein said solvent includes at least one solvent selected from the group consisting of isobornyl acetate and hydrocarbon terpene blends, the dye is N-[9-(2-carboxyphenyl)-6-diethylamino-3H-Xanthen-3-ylidene]-N-Ethylethanaminium Octadecanoate, and at least one of the proton donating compounds present is linalyl acetate.

* * * * *